US008175356B2

(12) United States Patent
Movassaghi et al.

(10) Patent No.: US 8,175,356 B2
(45) Date of Patent: May 8, 2012

(54) CARDIAC PHASE DETERMINATION

(75) Inventors: Babak Movassaghi, Denver, CO (US);
Michael Grass, Buchholz In Der Nordheide (DE); Dirk Schaefer, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 418 days.

(21) Appl. No.: 12/513,370

(22) PCT Filed: Oct. 24, 2007

(86) PCT No.: PCT/IB2007/054316
§ 371 (c)(1),
(2), (4) Date: May 4, 2009

(87) PCT Pub. No.: WO2008/053401
PCT Pub. Date: May 8, 2008

(65) Prior Publication Data
US 2010/0074485 A1 Mar. 25, 2010

(30) Foreign Application Priority Data
Nov. 3, 2006 (EP) .................................... 06123445

(51) Int. Cl.
*G06K 9/00* (2006.01)
(52) U.S. Cl. ........................................................ 382/128
(58) Field of Classification Search ................... 382/128
See application file for complete search history.

(56) References Cited

U.S. PATENT DOCUMENTS
| | | |
|---|---|---|
| 2002/0131545 A1* | 9/2002 | Hsieh ................................ 378/4 |
| 2004/0175024 A1 | 9/2004 | Rasche et al. |
| 2005/0033123 A1 | 2/2005 | Gardner et al. |
| 2005/0234331 A1 | 10/2005 | Sendai |
| 2006/0067459 A1 | 3/2006 | Boese et al. |
| 2007/0030946 A1* | 2/2007 | Tsuyuki et al. ................... 378/8 |

FOREIGN PATENT DOCUMENTS
| | | |
|---|---|---|
| EP | 0193712 A1 | 9/1986 |
| WO | 03094734 A2 | 11/2003 |
| WO | 2005008583 A2 | 1/2005 |

OTHER PUBLICATIONS

Manzke et al: "Automatic Phase Determination for Respectively Gated Cardiac CT"; Medical Physics, vol. 31, No. 12, Dec. 2004, pp. 3345-3362.
Movassaghi et al:"A Quantitative Analysis of 3D Coronary Modeling From Two or More Projection Images"; IEEE Transactions on Medical Imaging, vol. 23, No. 12, Dec. 3004, pp. 1517-1531.
Rasche et al: ECG-Gated Rotational Coronary Angiography (Abstract); RSNA, 83rd Scientific Session, 2003.
Blondel et al: "4-D Tomographic Representation of Coronary Arteries From One Rotational X-Ray Sequence"; Proc. MICCAI 2003, LNCS 2878, pp. 416-423, 2003.
Movassaghi et al:"3D Coronoary Reconstruction From Calibrated Motion-Conpensated 2D Projections Based on Semi-Automated Feature Point Detection"; Proceedings of SPIE, vol. 5370, pp. 1943-1950, 2004.
Movassaghi et al: "Automatic Gating Window Positioning for 3D Rotational Coronary Angiography"; Proceedings of SPIE, vol. 5370, pp. 1932-1942, 2004.
Rasche et al: "Automatic Selection of the Optimal Cardiac Phase for Gated Three-Dimensional Coronary X-Ray Angiography"; Academic Radiology, vol. 13, pp. 630-640, 2006.
Rasche et al ECG-Gated 3D-Rotational Coronary Angiography (3DRCA); Computer Assisted Radiology and Surgery 2002 Proceedings (CARS 2002),pp. 827-831.

* cited by examiner

*Primary Examiner* — Rodney Fuller

(57) ABSTRACT

For the reconstruction of the coronary arteries from rotational coronary angiography data, a crucial point is the selection of the optimal cardiac phase for data reconstruction. According to an exemplary embodiment of the present invention, an automatic approach for deriving optimal reconstruction windows is provided by fully automatically selecting the optimal cardiac phase on the basis of a delayed acquisition protocol where at least one heart phase needs to be acquired in a static projection geometry.

18 Claims, 6 Drawing Sheets

CARDIAC PHASE DETERMINATION

The invention relates to the field of medical imaging. In particular, the invention relates to an examination apparatus for examination of an object of interest, to a method of examination of an object of interest, an image processing device, a computer-readable medium and a program element.

Rotational angiography (RA) is a field of a growing interest. To enable a routinely clinical use of three-dimensional cardiac angiography (3D-RCA), either a significant reduction of required user interaction or the fully automatic generation of a three-dimensional coronary angiogram is required. Recently, initial work on new approaches for reduction of the required user-interaction has been presented. These approaches are based either on modelling [1] or on fully automatic non-motion compensated [2,3] or motion-compensated [4,5] reconstruction techniques.

Especially, the reconstruction-based approaches appear to be attractive, since they may fully automatically provide an accurate representation of the underlying anatomy. A major issue, especially in using non-motion compensated reconstruction techniques, is the selection of a proper cardiac phase, providing only little blur due to motion of the coronaries.

Recent publications [6,7] utilize the correlation between temporally successive volumes as an indicator for the inter-frame motion and suggest to select optimal cardiac phases according to the maximal values of the inter-frame correlation. Although, this method may have proven to provide valuable information on the current motion of the anatomy, it may not directly provide a measure for the image quality of a certain frame.

In [8] a method is presented to derive an image quality analysis of single temporal snapshots based on histogram analysis of the respective three-dimensional reconstructed image. This method, however, requires the generation of time consuming multiple three-dimensional reconstructed images in all cardiac phases to determine the optimal cardiac phase by comparison of the image quality index.

It would be desirable to provide for an improved determination of a cardiac phase for image reconstruction in coronary angiography.

According to an exemplary embodiment of the present invention, an examination apparatus for examination of an object of interest is provided, the examination apparatus comprising an acquisition unit adapted for acquiring a series of projection images of the object of interest on the basis of a delayed acquisition trajectory, and a determination unit adapted for determining a first subtracted image and a second subtracted image on the basis of the series of projection images, wherein the determination unit is further adapted for determining a cardiac phase for data reconstruction on the basis of the first subtracted image and the second subtracted image.

Therefore, the examination apparatus may be adapted for performing an extraction of the optimal cardiac phase based on the analysis of two-dimensional projection images of CA (contrast agent) filled coronary arteries acquired in static angular position over (at least) one cardiac cycle. This may result in a fast and sophisticated selection of the optimal cardiac phase, providing only little blur due to cardiac motion.

According to another exemplary embodiment of the present invention, the series of projection images comprises a first, a second, a third and a fourth projection image, wherein the first subtracted image corresponds to a subtraction of the second projection image from the first projection image, and wherein the second subtracted image corresponds to a subtraction of the fourth projection image from the third projection image.

Thus, by simply subtracting different images of the heart from each other (the images being acquired in a static acquisition mode), the optimal cardiac phase may be determined.

According to another exemplary embodiment of the present invention, the first and the second images are subsequent images and the third and the fourth images are subsequent images.

Therefore, only images which are acquired directly after each other are subtracted from each other.

According to another exemplary embodiment of the present invention, wherein the determination unit is further adapted for determining a first variance value corresponding to the first subtracted image and a second variance value corresponding to the second subtracted image, and wherein the cardiac phase for data reconstruction corresponds to the subtracted image having the lower variance value.

Thus, according to this exemplary embodiment of the present invention, the variance of each subtracted projection image is calculated and the calculated variances are compared to each other. The lowest variance then determines the cardiac phase used for image reconstruction.

According to another exemplary embodiment of the present invention, the cardiac phase for data or image reconstruction is determined fully automatically.

Therefore, no user-interaction may be necessary for determining the most appropriate time window.

According to another exemplary embodiment of the present invention, the examination apparatus further comprises an electrocardiogram, wherein the data reconstruction is an electrocardiogram-gated three-dimensional coronary data reconstruction.

According to a further exemplary embodiment of the present invention, the series of projection images for determining the cardiac phase for data reconstruction is acquired in a static projection geometry over one cardiac cycle.

Thus, all images which are needed for the determination of the optimal cardiac phase are acquired during one single cardiac cycle, followed by a standard rotational data acquisition scheme. Alternatively, the standard rotational data acquisition scheme may be performed before the acquisition of the reference images in the static projection geometry.

Therefore, time-consuming interactive selection of the optimal cardiac phase by visual inspection of multiple high-resolution data sets reconstructed at different cardiac phases may be avoided by providing an automatic scheme for deriving an optimal reconstruction phase.

According to another exemplary embodiment of the present invention, the examination apparatus is adapted as one of a three-dimensional computed tomography apparatus and a three-dimensional rotational X-ray apparatus.

It should be noted in this context, that the present invention is not limited to computed tomography or rotational angiography, but may always then be applied when an appropriate reconstruction phase for imaging of periodically moving objects has to be determined.

According to another exemplary embodiment of the present invention, the examination apparatus is configured as one of the group consisting of a material testing apparatus, a medical application apparatus and a micro CT system.

According to another exemplary embodiment of the present invention, the determination unit is further adapted for determining a width of a gating window for data reconstruction on the basis of a series of subtraction images.

A field of application of the invention may be medical imaging, in particular cardiac imaging.

Furthermore, according to another exemplary embodiment of the present invention, a method of examination of an object of interest with an examination apparatus is provided, the method comprising the steps of acquiring a series of projection images of the object of interest on the basis of a delayed acquisition trajectory, determining a first subtracted image and a second subtracted image on the basis of the series of projection images and determining a cardiac phase for data reconstruction on the basis of the first subtracted image and the second subtracted image.

Furthermore, according to another exemplary embodiment of the present invention, the method comprises the steps of determining a first variance of the first subtracted image and a second variance of the second subtracted image and comparing the first variance with the second variance, wherein the cardiac phase for data reconstruction corresponds to the projection image corresponding to the lower variance of the first variance and the second variance.

In other words, after a static projection image acquisition, subtracted images of subsequent projections of the static projections are created and the variance of each subtracted projection image is calculated. After that, the cardiac phase corresponding to the projection belonging to the lowest variance value is determined.

According to another exemplary embodiment of the present invention, an image processing device is provided, which comprises a memory for storing a series of projection images of the object of interest acquired on the basis of a delayed acquisition trajectory and a determination unit adapted for determining a first subtracted image and a second subtracted image on the basis of the series of projection images, wherein the determination unit is further adapted for determining a cardiac phase for data reconstruction on the basis of the first subtracted image and the second subtracted image.

Furthermore, according to another exemplary embodiment of the present invention, a computer-readable medium is provided, in which a computer program for examination of an object of interest is stored which, when executed by a processor, causes the processor to carry out the above-mentioned method steps.

Furthermore, according to another exemplary embodiment of the present invention, a program element for examination of an object of interest is provided, which, when being executed by a processor, causes the processor to carry out the above-mentioned method steps.

The method of examination of the object of interest may be embodied as the computer program, i.e. by software, or may be embodied using one or more special electronic optimization circuits, i.e. in hardware, or the method may be embodied in hybrid form, i.e., by means of software components and hardware components.

The program element according to an embodiment of the invention is preferably loaded into working memories of a data processor. The data processor may thus be equipped to carry out embodiments of the methods of the present invention. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

It may be seen as the gist of an exemplary embodiment of the present invention that an examination apparatus is provided which is adapted for selecting an optimal cardiac phase in a fully automatically manner on the basis of a delayed acquisition protocol in which at least one heart phase is acquired in a static projection geometry. This may provide for a fast and sophisticated selection of an optimal cardiac phase, resulting in minimal blur due to cardiac motion.

These and other aspects of the present invention will become apparent from and elucidated with reference to the embodiments described hereinafter.

Exemplary embodiments of the present invention will be described in the following, with reference to the following drawings.

The illustration in the drawings is schematic. In different drawings, similar or identical elements are provided with the same reference numerals.

Figure 1:
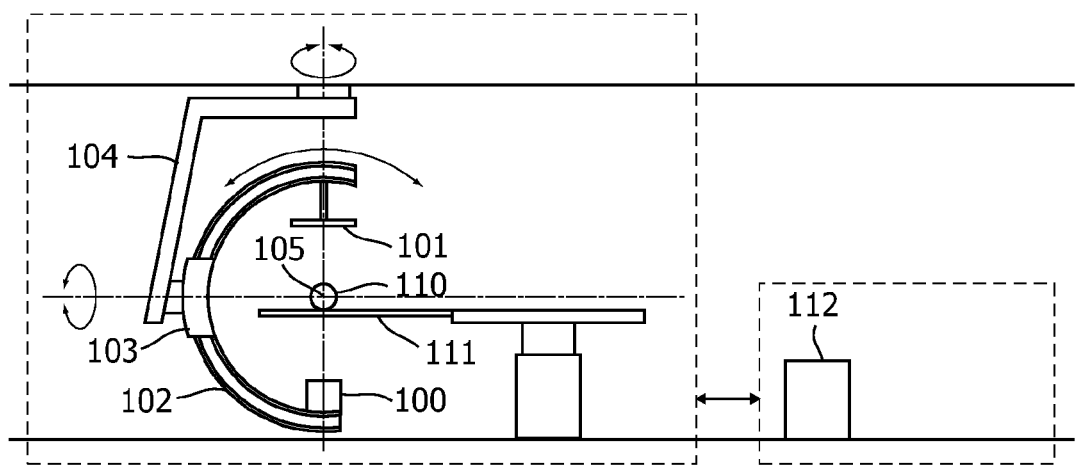
FIG. 1 shows a schematic representation of a rotational X-ray scanner according to an exemplary embodiment of the present invention.

FIG. 1 shows a schematic representation of an exemplary rotational X-ray scanner according to an exemplary embodiment of the present invention. An X-ray source 100 and a flat detector 101 with a large sensitive area are mounted to the ends of a C-arm 102. The C-arm 102 is held by a curved rail, the "sleeve" 103. The C-arm can slide in the sleeve 103, thereby performing a "roll movement" about the axis of the C-arm. The sleeve 103 is attached to an L-arm 104 via a rotational joint and can perform a "propeller movement" about the axis of this joint. The L-arm 104 is attached to the ceiling via another rotational joint and can perform a rotation about the axis of this joint. The various rotational movements are affected by servomotors. The axes of the three rotational movements and the cone-beam axis always meet in a single fixed point, the "isocentre" 105 of the rotational X-ray scanner. There is a certain volume around the isocentre that is projected by all cone-beams along the source trajectory. The shape and size of this volume of projection depend on the shape and size of the detector and on the source trajectory. In FIG. 1, the ball 110 indicates the biggest isocentric ball that fits into the volume of projection. The object (for example a patient or an item of baggage) to be imaged is placed on the table 111 such that the object's volume of interest fits in the volume of projection. The volume of projection therefore limits the size of the volume of interest.

The various rotational movements are controlled by a control unit 112. Each triple of C-arm angle, sleeve angle, and L-arm angle defines a position of the X-ray source. By varying these angles with time, the source can be made to move along a prescribed source trajectory. The detector at the other end of the C-arm makes a corresponding movement. The source trajectory will be confined to the surface of an isocentric sphere.

In the following, a fully automatically extraction of the optimal cardiac phase for ECG-gated three-dimensional coronary reconstruction (3D-CR), based on the analysis of two-dimensional projection images of CA field coronary angiograms acquired in static angular position over (at least) one cardiac cycle according to an exemplary embodiment of the present invention is described.

Figure 6:
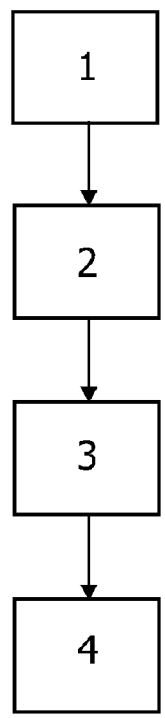
FIG. 6 shows a flow-chart of an exemplary method according to the present invention.

FIG. 6 shows a flow-chart of an exemplary method according to the present invention for examining an object of interest (and, of course, for determining the optimal cardiac phase). The method is based on a delayed acquisition protocol where at least one heart phase needs to be acquired in a static view. The method to extract the optimal cardiac phase may be described in four major steps:

In step 1, a series of projection images is acquired in a static setup. The images are projection images of CA filled coronary arteries based on a delayed acquisition trajectory.

Then, in step 2, subtracted images of subsequent projections of the static projections are created. In step 3, the variance of each subtracted projection image is calculated and in step 4, the cardiac phase corresponding to the projection belonging to the lowest variance value is determined.

Figure 2:
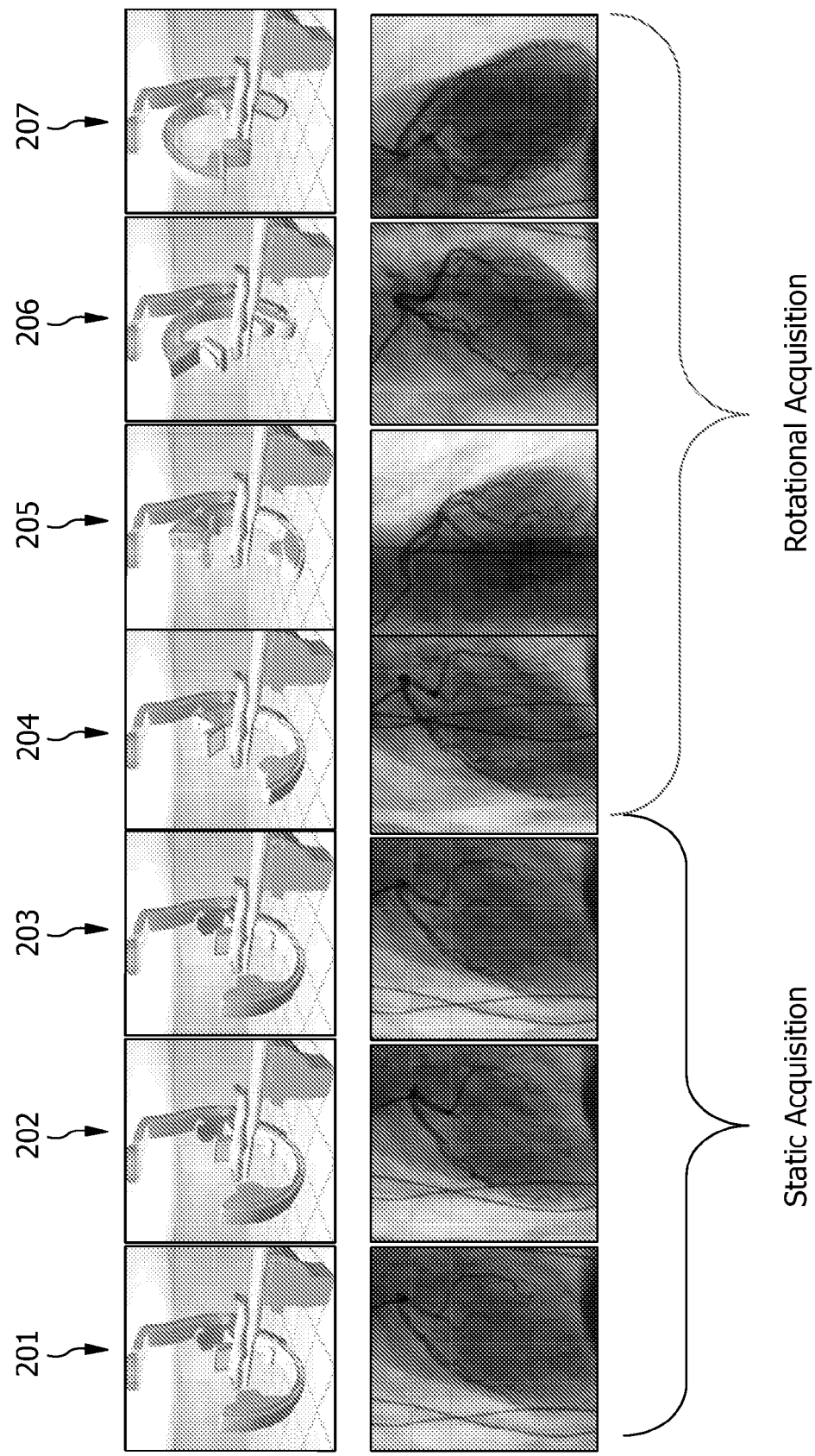
FIG. 2 shows a schematic representation of a delayed acquisition trajectory.

FIG. 2 shows a schematic representation of a delayed acquisition trajectory. The C-arm X-ray system starts to rotate (see reference numeral 204) approximately after 1 to 1.5 seconds after starting the data acquisition. It should be noted however, if the data acquisition is performed in a faster acquisition mode, the start of the rotation may be earlier. During the static acquisition (see reference numerals 201, 202, 203), the series of projection images for determining the optimal cardiac phase is acquired. During the following standard acquisition process (see reference numerals 204, 205, 206, 207) the C-arm system rotates.

The lower row of images depicting coronary arteries corresponds to the positions of the C-arm system depicted in the upper row of images.

Figure 3:
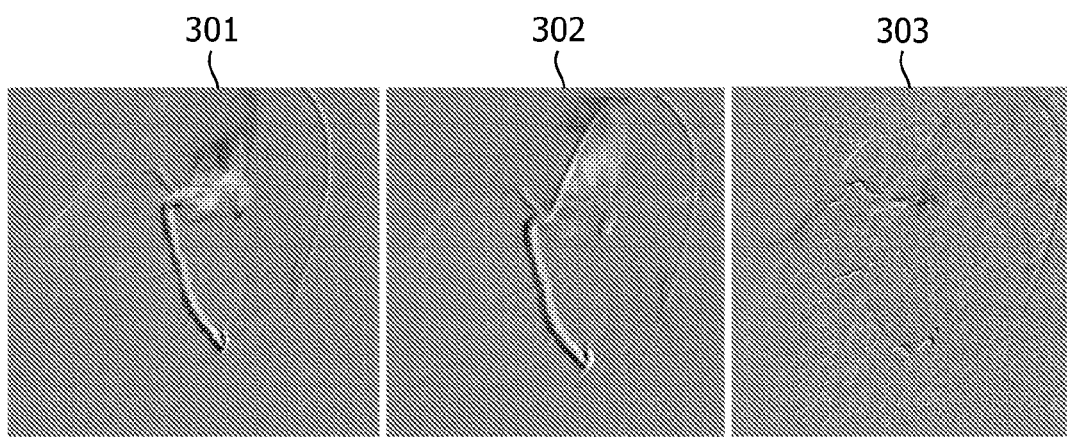
FIG. 3 shows three subtracted images of subsequent projection images.

FIG. 3 shows three subtracted images 301, 302, 303 of subsequent projection images. The variance of subtracted angiograms of two subsequent projections, acquired during a rotational run, correlates to the cardiac motion. Therefore, large variance values correspond to subsequent projection images with large motion in between the acquisition (see images 301, 302). On the other hand, small variance values correspond to small motion (see image 303).

Figure 4A:
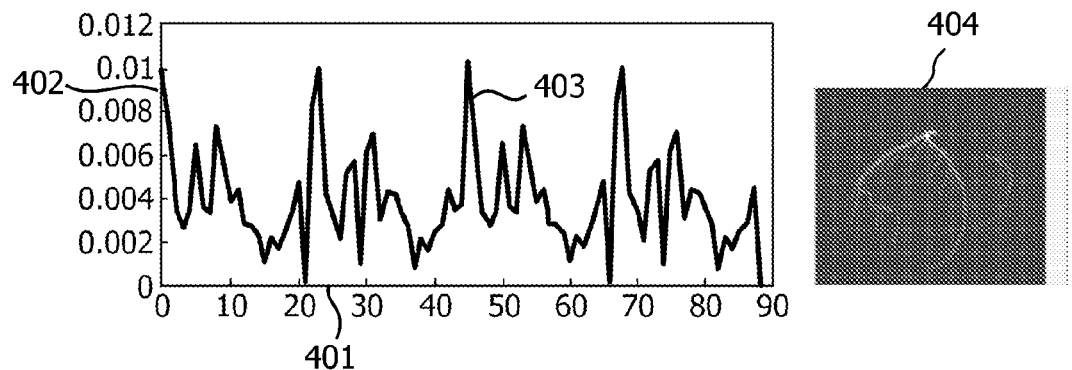
FIG. 4a shows a schematic representation of three exemplary plots of variance values of the subtracted projection images for a data set corresponding to a phantom.
Figure 4B:
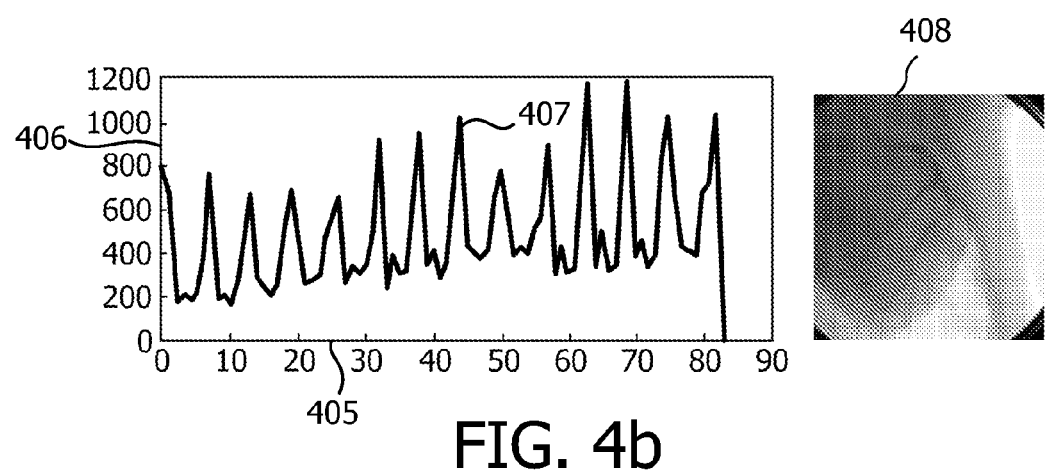
FIG. 4b shows a schematic representation of three exemplary plots of variance values of the subtracted projection images for data set corresponding to an animal.
Figure 4C:
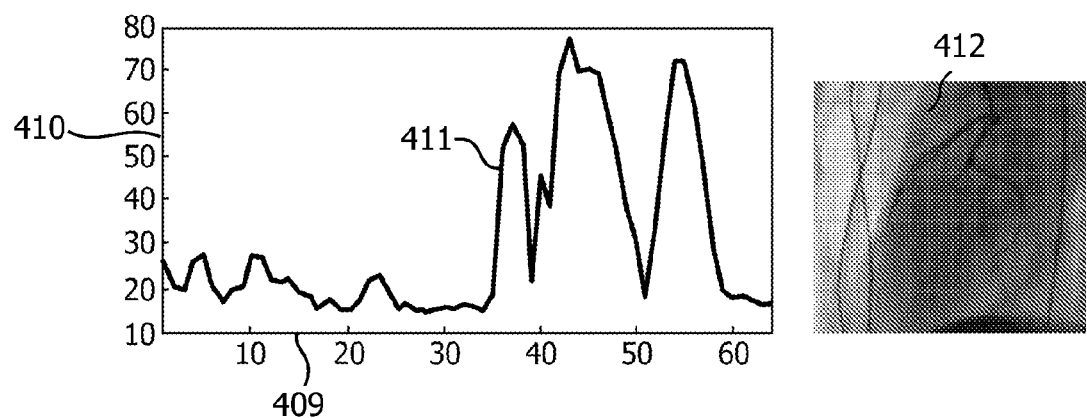
FIG. 4c shows a schematic representation of three exemplary plots of variance values of the subtracted projection images for a data set corresponding to a human.

FIG. 4 shows an illustration of exemplary plots of variance values of the subtracted projection images for a phantom (FIG. 4a), an animal (FIG. 4b) and a human (FIG. 4c) data set. Optimal cardiac phases correspond to minimum variance values.

The horizontal axes 401, 405 and 409 correspond to the cardiac phase and range from 0 to 90° in case of FIG. 4a, 4b and from 0 to approximately 65° in case of FIG. 4c. The vertical axes 402, 406 and 410 correspond to the variance (in arbitrary units).

Plot 403 shows the variance relating to the phantom 404, plot 407 shows the variance relating to an animal 408 and plot 411 shows the variance relating to a human heart 412.

Figure 5:
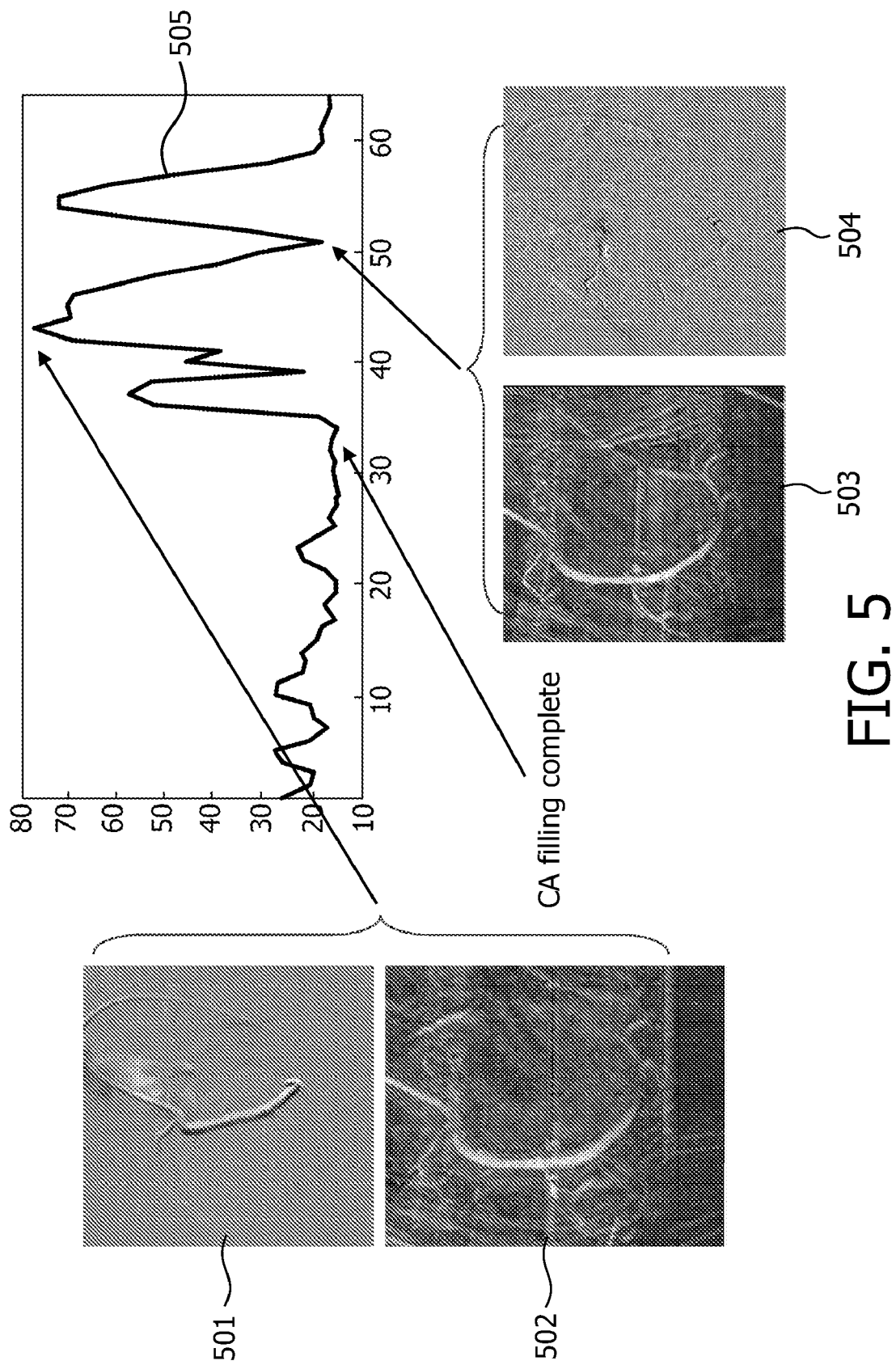
FIG. 5 shows results of maximum intensity projection images of gated three-dimensional reconstructed volume images.

FIG. 5 shows the results of maximum intensity projection images of gated three-dimensional reconstructed volume images corresponding to maximum (501, 502) and minimum (503, 504) variance values. The corresponding variance values are depicted in plot 505.

An exemplary implementation of the invention may be vascular interventions where rotational acquisition is utilized. In particular, the invention may be implemented in the field of gated three-dimensional coronary reconstruction and motion compensated coronary reconstruction.

Figure 7:
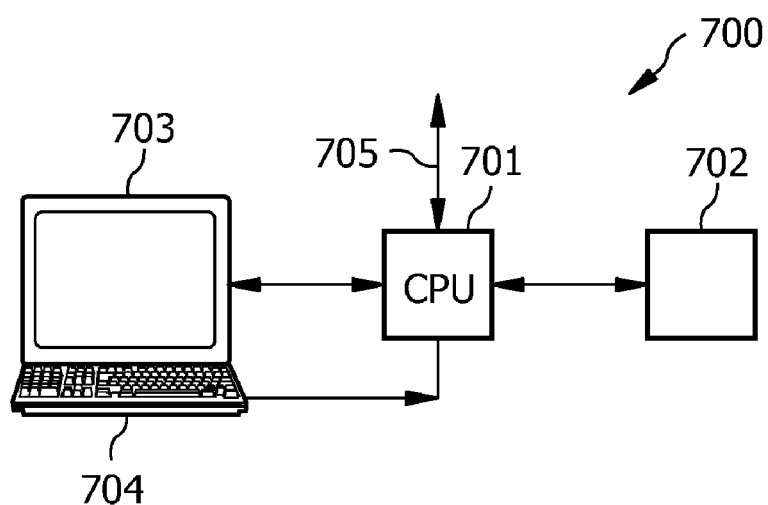
FIG. 7 shows an exemplary embodiment of an image processing device according to the present invention for executing an exemplary embodiment of a method in accordance with the present invention.

FIG. 7 shows an exemplary embodiment of a data processing device 700 according to the present invention for executing an exemplary embodiment of a method in accordance with the present invention.

The data processing device 700 depicted in FIG. 7 comprises a central processing unit (CPU) or image processor 701 connected to a memory 702 for storing an image depicting an object of interest, such as a patient or an item of baggage. The data processor 701 may be connected to a plurality of input/output network or diagnosis devices, such as a X-ray C-arm apparatus. The data processor 701 may furthermore be connected to a display device 703, for example, a computer monitor, for displaying information or an image computed or adapted in the data processor 701. An operator or user may interact with the data processor 701 via a keyboard 704 and/or other input or output devices, which are not depicted in FIG. 7.

Furthermore, via the bus system 705, it may also be possible to connect the image processing and control processor 701 to, for example, a motion monitor, which monitors a motion of the object of interest. In case, for example, a lung of a patient is imaged, the motion sensor may be an exhalation sensor. In case the heart is imaged, the motion sensor may be an electrocardiogram.

Exemplary embodiments of the invention may be sold as a software option to CT scanner console, imaging workstations or PACS workstations.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

Literature Listing

[1] Movassaghi B, Rasche V, Grass M, Viergever M, Niessen W, "A quantitative analysis of 3D coronary modeling from two or more projection images", IEEE Trans. Med. Imag., vol. 12, no. 23, pp. 1517-1531, 2004.

[2] Rasche V, Buecker A, Grass M, Koppe R, Op de Beek J, Bertrams R, Suurmond R, Kuehl H, Guenther R W. Ecg-gated 3Drotational coronary angiography (3DRCA), in Computer Assisted Radiology and Surgery 2002 Proceedings (CAR '02). 2002, pp. 827-831, Springer.

[3] Rasche V, Buecker A, Grass M, Suurmond R, Koppe R. Kuehl H. ECG-gated 3D Rotational Coronary Angiography, RSNA, 83rd Scientific Session, 2003

[4] Blondel C, Malandain G, Vaillant R, et al. 4-D Tomographic representation of coronary arteries from one rotational X-ray sequence, Proc. MICCAI 2003, LNCS 2878, 416-423 (2003)

[5] Movassaghi B, Rasche V, Viergever M. A, Niessen W. J, "3D coronary reconstruction from calibrated motion-compensated 2D projections based on semi-automated feature point detection", in Proc. SPIE Medical Imaging: Image Processing, vol. 5370, San Diego, Calif., pp. 1943-1950, 2004.

[6] Movassaghi B, Istel T, Rasche V, "Automatic gating window positioning for 3D rotational coronary angiography (3DRCA)", in Proc. SPIE Medical Imaging: Image Processing, vol. 5370, San Diego, Calif., pp. 1932-1942, 2004.

[7] Manzke R, Nielsen T. and Köhler Th, Hawkes D, Grass M, "Automatic phase determination for retrospectively gated cardiac CT", Medical Physics, Vol. 31(12), 3345-3362, 2004.

[8] Volker Rasche, Babak Movassaghi, Michael Grass, Dirk Schaefer, Arno Buecker, Automatic Selection of the Optimal Cardiac Phase for Gated Three-Dimensional Coronary X-Ray Angiography, Academic Radiology, Vol. 13, 630-640, 2006.

The invention claimed is:

1. An examination apparatus for examination of an object of interest, the examination apparatus comprising:
    an acquisition unit which acquires, in a static projection geometry over one cardiac cycle, a series of projection images of the object of interest on a basis of a delayed acquisition trajectory; and
    a determination unit which determines a first subtracted image and a second subtracted image on a basis of the series of projection images;
    wherein the determination unit further determines a cardiac phase for data reconstruction on a basis of the first subtracted image and the second subtracted image.

2. The examination apparatus of claim 1,
    wherein the series of projection images comprises a first, a second, a third and a fourth projection image;
    wherein the first subtracted image corresponds to a subtraction of the second projection image from the first projection image; and
    wherein the second subtracted image corresponds to a subtraction of the fourth projection image from the third projection image.

3. The examination apparatus of claim 1,
    wherein the first and the second images and wherein the third and the fourth images are subsequent images.

4. The examination apparatus of claim 1,
    wherein the determination unit further determines a first variance value corresponding to the first subtracted image and a second variance value corresponding to the second subtracted image;
    wherein the cardiac phase for data reconstruction corresponds to the subtracted image having the lower variance value.

5. The examination apparatus of claim 1,
    wherein the cardiac phase for data reconstruction is determined fully automatically.

6. The examination apparatus of claim 1,
    further comprising an electrocardiogram;
    wherein the data reconstruction is an ECG-gated 3D coronary data reconstruction.

7. The examination apparatus of claim 6,
    wherein the acquisition unit rotationally acquires a series of projection images of the object of interest subsequent to the acquisition of the static series of projection images, and wherein the data reconstruction is in accordance with the rotationally acquired series of projection images and the determined cardiac phase.

8. The examination apparatus of claim 7, wherein the acquisition unit is adapted acquire the static series of projection images during a preselected delay associated with the delayed acquisition trajectory, and wherein the image acquisition unit is adapted for rotationally acquiring the series of projection images of the object of interest after the preselected delay.

9. The examination apparatus of claim 1, wherein the projection images are acquired by a three-dimensional rotational angiography X-ray apparatus.

10. The examination apparatus of claim 9, wherein the three-dimensional rotational angiography X-ray apparatus includes:
    a C-arm which supports an X-ray source and a flow panel X-ray detector.

11. The examination apparatus of claim 1,
    wherein the determination unit further determines a width of a gating window for data reconstruction on a basis of a series of subtraction images.

12. A method of examination of an object of interest with an examination apparatus, method comprising the steps of:
    with a C-arm scanner, acquiring a series of 2-D projection images of the object of interest with the C-arm scanner stationary;
    determining, with one or more processors, a first subtracted image and a second subtracted image by subtracting immediately adjacent 2-D projection images of the series of 2-D projection images acquired with the scanner stationary; and
    determining a cardiac phase for data reconstruction on a basis of the first subtracted image and the second subtracted image;
    rotating the C-arm scanner around the object of interest in a series of steps; and
    at each step, in the determined cardiac phase, acquiring a 2-D projection image of the object of interest.

13. The method of claim 12, further comprising the steps of:
    determining a first variance of the first subtracted image and a second variance of the second subtracted image; and
    comparing the first variance with the second variance;
    wherein the cardiac phase for data reconstruction corresponds to the projection image corresponding to the lower variance of the first variance and the second variance.

14. The method of claim 13,
    wherein the static series of projection images comprises a first image immediately temporally adjacent to a second image, the second image immediately temporally adjacent to a third image, and a third image immediately temporally adjacent to a fourth image;
    wherein the first subtracted image corresponds to a subtraction of the second projection image from the first projection image; and
    wherein the second subtracted image corresponds to a subtraction of the fourth projection image from the third projection image.

15. The method of claim 12, further comprising:
    reconstructing the rotationally acquired series of 2-D projection images corresponding to the determined cardiac phase into a 3-D rotational angiography image.

16. The method of claim 12, wherein the static series of projection images are acquired subsequent to the acquisition of the rotational series of projection images.

17. An image processing device, the image processing device comprising:
    a memory for storing a first series of projection images of an object of interest acquired in a static projection geometry on a basis of a delayed acquisition trajectory, and a second series of projection images of the object of interest acquired in a rotational projection operation;
    a processor programmed to:
        determine a plurality of subtracted images corresponding to a first subtracted image and a second subtracted image using the series of projection images acquired in the static projection geometry; and calculate a first variance associated with the first subtracted image and a second variance associated with the second subtracted image;

determine a cardiac phase for data reconstruction based upon a comparison of the first calculated variance to the second calculated variance.

18. A non-transitory computer-readable medium carrying computer code which, controls one or more processors to:

control a C-arm scanner to acquire a static series of projection images of an object of interest with the C-arm static;

determine a first subtracted image and a second subtracted image on a basis of the static series of projection images;

determine a cardiac phase for data reconstruction on a basis of the first subtracted image and the second subtracted image; and control the C-arm scanner to acquire a rotational series of projection images in the determined cardiac phase while the C-arm is moving around the object.

* * * * *